United States Patent [19]

Pommer et al.

[11] 4,083,986

[45] Apr. 11, 1978

[54] 2-TRICHLOROMETHYL-1,3,4-THIADIAZOLE

[75] Inventors: Ernst-Heinrich Pommer, Limburgerhof; Helmut Hagen; Helmut Fleig, both of Frankenthal, all of Germany

[73] Assignee: BASF Aktiengesellschaft, Rheinland-Pfalz, Germany

[21] Appl. No.: 807,400

[22] Filed: Jun. 17, 1977

Related U.S. Application Data

[63] Continuation of Ser. No. 614,193, Sep. 17, 1975, abandoned.

[30] Foreign Application Priority Data

Oct. 4, 1974 Germany .............................. 2447387

[51] Int. Cl.$^2$ .................. A61K 31/425; C07D 285/12

[52] U.S. Cl. ................................ 424/270; 260/302 D
[58] Field of Search ..................... 424/270; 260/302 D

[56] References Cited

PUBLICATIONS

Miyata et al., Kyoto Furitsu Daigaku Gakujutsu Hokoku, Nogako, 1973, (25), pp. 30–36.
Chemical Abstracts, vol. 80, Chemical Substance Index, "1,3,4-Thiadiazole".

*Primary Examiner*—Richard J. Gallagher
*Attorney, Agent, or Firm*—Keil, Thompson & Shurtleff

[57] ABSTRACT

The new compound 2-trichloromethyl-1,3,4-thiadiazole, a process for its manufacture, a fungicide containing this compound as active ingredient, and a process for controlling fungi with this compound.

10 Claims, No Drawings

2-TRICHLOROMETHYL-1,3,4-THIADIAZOLE

This is a continuation of application Ser. No. 614,193, filed Sept. 17, 1975, now abandoned.

The present invention relates to the new compound 2-trichloromethyl-1,3,4-thiadiazole, a process for its manufacture, a fungicide containing this compound, and its use as a fungicide.

It is known that 1,3,4-thiadiazoles are destroyed by oxidants under drastic reaction conditions, e.g., the sulfur in 1,3,4-thiadiazole is oxidized to the sulfate by 30% $H_2O_2$ (J. Goerdeler, J. Ohm and O. Tegtmayer, Ber., 89, 1534-43, 1956). It is also known that the ring system can also be hydrolytically destroyed under drastic conditions, e.g., at 100° C already, hydrazine sulfate forms from 2,5-dimethyl-1,3,4-thiadiazole in dilute sulfuric acid (Beilstein, Handbuch der Organischen Chemie, 27, 565).

We have now found that the new compound 2-trichloromethyl-1,3,4-thiadiazole of the formula

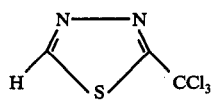

is obtained when 2,5-bis-trichloromethyl-1,3,4-thiadiazole is reacted with concentrated sulfuric acid at elevated temperature.

In view of the art it was surprising how stable the thiadiazole ring in 2,5-bis-trichloromethyl-1,3,4-thiadiazole or 2-trichloro-methyl-1,3,4-thiadiazole is in concentrated sulfuric acid at temperatures in the vicinity of 200° C, where concentrated sulfuric acid already has a strong oxidative action. Under these reaction conditions only a trichloromethyl group is eliminated. The reaction is illustrated by the following equation:

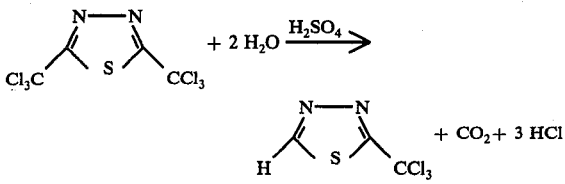

The 2,5-bis-trichloromethyl-1,3,4-thiadiazole used as starting material is easily accessible in high yields and purity by chlorination of 2,5-dimethyl-1,3,4-thiadiazole in glacial acetic acid (German Laid-Open Application DOS 2,253,863).

The reaction of the invention is generally carried out at temperatures of from 150° to 220° C, preferably 170° to 200° C, at atmospheric, sub- or superatmospheric pressure, and continuously or batchwise. The concentration of the sulfuric acid is from 70 to 99wt%, preferably from 85 to 98wt%. The reaction period is from 0.01 to 5 hours, preferably 0.05 to 0.5 hours. The reaction mixture is worked up by pouring it on to ice, whereupon the product precipitates out.

The reaction may be carried out as follows. 2,5-bis-trichloromethyl-1,3,4-thiadiazole is heated at 170° to 180° C in 4 to 5 times its weight of sulfuric acid of suitable concentration for about 15 minutes, and the reaction mixture is then poured on to ice; the precipitated solid is suction filtered and washed with water. Generally, the reaction product is so pure that no more purification steps are necessary. If the reaction is incomplete, the product may easily be separated from unreacted starting material by extraction with methanol, in which 2-trichloromethyl-1,3,4-thiadiazole is, in contrast to 2,5-bis-trichloromethyl-1,3,4-thiadiazole, readily soluble.

The compound of the invention is fungicidally effective, especially on mildews, e.g., Aspergillus niger, and Basidiomycetes, e.g., Rhizoctonia solani and Coniophora cerebella. The compound maybe used for protecting not only plants but also materials. The active ingredient may also be mixed with other fungicides, which often results in a widening of the fungicidal range of action. The compound also has a good herbicidal action on Echinochloa crus-galli (germination stage) and is effective as a chemical sterilization agent for Dysdercus.

The process according to the invention is illustrated by the following examples. Parts in the examples are by weight, and they bear the same relationship to parts by volume as kilograms to liters.

EXAMPLE 1

A mixture of 6.4 parts of 2,5-bis-trichloromethyl-1,3,4-thiadiazole and 30 parts by volume of 91% sulfuric acid is heated for 0.1 hour at from 175° to 185° C. The reaction mixture is then carefully poured on to ice and the precipitated solid is suction filtered. The product is washed with water and treated with 20 parts by volume of methanol, and small amounts of undissolved starting material are filtered off. After concentration of the methanolic solution there is obtained 3.4 parts (83% of theory) of 2-trichloromethyl-1,3,4-thiadiazole; m.p.: 58° C.

EXAMPLE 2

At 180° to 190° C and over a period of 0.1 hour, a solution of 160.5 parts of 2,5-bis-trichloromethyl-1,3,4-thiadiazole in 200 parts by volume of concentrated $H_2SO_4$ is introduced into 100 parts by volume of concentrated $H_2SO_4$. The mixture is heated at 170° to 180° C for 0.15 hour, and then poured on to 2,000 parts of ice. The precipitated solid is suction filtered and washed with water. There is obtained 94 parts (92% of theory) of 2-trichloromethyl-1,3,4-thiadiazole; m.p.:57° C.

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coaltar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in all oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts or fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol ethers, lignin, sulfite waste liquors and methyl cellulose.

Powders, dusts and broadcasting agents may be prepared by mixing or grinding the active ingredients with a solid carrier.

Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

EXAMPLE 3

Aspergillus test

The active ingredients are added to a nutrient solution optimally suited for promoting the growth of the fungus Aspergillus niger in amounts of 100, 75, 50, 25 and 10 parts by weight per million parts of nutrient solution. 20 ml of the nutrient solution prepared in this manner is placed in 100 ml Erlenmeyer flasks and then inoculated with 0.3 mg of Aspergillus spores. The flasks are heated for 120 hours at 36° C and the extent of fungus spread - predominantly on the surface of the nutrient solution - is assessed.

| Active ingredient | Amount of active ingredient in parts per million parts of nutrient solution | | | | |
|---|---|---|---|---|---|
| | 100 | 75 | 50 | 25 | 10 |
| ![structure] Cl₃C–(N=N)–S–H | 0 | 0 | 0 | 2 | 3 |
| tetramethylthiuram disulfide (prior art) | 1 | 2 | 2 | 4 | 5 |

| Active ingredient | Amount of active ingredient in parts per million parts of nutrient solution | | | | |
|---|---|---|---|---|---|
| | 100 | 75 | 50 | 25 | 10 |
| control (untreated) | | | 5 | | |

0 = no fungus growth, graduated down to
5 = uncontrolled growth (surface of nutrient solution completely covered by fungus)

EXAMPLE 4

Cotton seeds of the "Delta Pine" variety are thoroughly dusted with a dressing consisting of 40% (by weight) of active ingredient and 60% of talc, in an amount of 0.3 g per 100 g of seeds. These seeds are placed in pots and covered with soil which has been artificially inoculated with the fungus Rhizoctonia solani. After 21 days the following results are obtained:

| Active ingredient | Percentage of cotton plants attacked (21 days after emergence) |
|---|---|
| Cl₃C–(N=N)–S–H | 2 |
| H₂C–O–C(CH₃)=C(S)–CO–NH–C₆H₅ (prior art) | 15 |
| control (untreated) | 90 |

EXAMPLE 5

90 parts by weight of the compound of Example 1 is mixed with 10 parts by weight of N-methyl-α-pyrrolidone. A mixture is obtained which is suitable for application in the form of very fine drops.

EXAMPLE 6

20 parts by weight of the compound of Example 1 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 7

20 parts by weight of the compound of Example 1 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 8

20 parts by weight of the compound of Example 2 is dissolved in a mixture consisting of 25 parts by weight of cyclohexanol, 65 parts by weight of a mineral oil fraction having a boiling point between 210° and 280° C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 9

20 parts by weight of the compound of Example 2 is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 10

3 parts by weight of the compound of Example 1 is intimately mixed with 97 parts by weight of particulate kaolin. A dust is obtained containing 3% by weight of the active ingredient.

EXAMPLE 11

30 parts by weight of the compound of Example 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

We claim:

1. 2-trichloromethyl-1,3,4-thiadiazole.
2. A process for controlling fungi which comprises treating the objects to be protected against attack by fungi with a fungicidal amount of 2-trichloromethyl-1,3,4-thiadiazole.
3. A process as claimed in claim 2 wherein the fungi controlled by said treatment are selected from the class consisting of mildews and Basidiomycetes.
4. A process as claimed in claim 3 wherein the fungus from the mildew class is Aspergillus niger.
5. A process as claimed in claim 3 wherein the fungi from the Basidiomycetes class are Rhizoctonia solani and Coniophora cerebella.
6. A fungicidal composition comprising a liquid or solid carrier and from 0.02 to 95% by weight of 2-trichloromethyl-1,3,4-thiadiazole as an active fungicidal component.
7. A fungicidal composition as claimed in claim 6 wherein the fungicidal composition contains from 0.1 to 95% by weight of fungicidal component.
8. A fungicidal composition as claimed in claim 6 wherein the carrier is water in which the active component is dispersed.
9. A fungicidal composition as claimed in claim 6 in the form of a concentrate dilutable with water and containing, in addition to the active component, a dispersing or emulsifying agent.
10. A fungicidal composition as claimed in claim 6 wherein the carrier is mineral oil or an aromatic hydrocarbon in which the active component is dissolved.

* * * * *